US008593107B2

(12) United States Patent
Penner et al.

(10) Patent No.: US 8,593,107 B2
(45) Date of Patent: Nov. 26, 2013

(54) METHODS AND SYSTEMS FOR RECHARGING AN IMPLANTED DEVICE BY DELIVERING A SECTION OF A CHARGING DEVICE ADJACENT THE IMPLANTED DEVICE WITHIN A BODY

(75) Inventors: Avi Penner, Tel Aviv (IL); Eyal Doron, Kiriat-Yam (IL); Jeffrey E. Stahmann, Ramsey, MN (US); Keith R. Maile, New Brighton, MN (US); Binh C. Tran, Minneapolis, MN (US); Wangcai Liao, Houston, TX (US); Bin Mi, Plymouth, MN (US); Paul J. Huelskamp, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 967 days.

(21) Appl. No.: 12/605,579

(22) Filed: Oct. 26, 2009

(65) Prior Publication Data

US 2010/0106028 A1    Apr. 29, 2010

Related U.S. Application Data

(60) Provisional application No. 61/108,635, filed on Oct. 27, 2008.

(51) Int. Cl.
*H01M 10/44* (2006.01)
(52) U.S. Cl.
USPC ........................................................ 320/114
(58) Field of Classification Search
USPC ........... 320/107, 108, 112, 114, 115; 607/2, 5
See application file for complete search history.

(56) References Cited

U.S. PATENT DOCUMENTS

| 2,786,899 | A | 3/1957 | Carlisle et al. |
| 3,536,836 | A | 10/1970 | Pfeiffer |
| 3,672,352 | A | 6/1972 | Summers |
| 3,757,770 | A | 9/1973 | Brayshaw et al. |
| 3,805,796 | A | 4/1974 | Terry, Jr. et al. |
| 3,853,117 | A | 12/1974 | Murr |
| 3,943,915 | A | 3/1976 | Severson |
| 3,970,987 | A | 7/1976 | Kolm |
| 4,026,276 | A | 5/1977 | Chubbuck |

(Continued)

FOREIGN PATENT DOCUMENTS

| EP | 0 499 939 | 8/1992 |
| EP | 0 928 598 | 12/1998 |

(Continued)

OTHER PUBLICATIONS

Harrison et al., "A Low-Power Low-Noise CMOS Amplifier for Neural Recording Applications," IEEE Journal of Solid-State Circuits 38(6):958-965, Jun. 2003.

(Continued)

*Primary Examiner* — Edward Tso
(74) *Attorney, Agent, or Firm* — Faegre Baker Daniels LLP

(57) ABSTRACT

Methods, systems, and apparatus for recharging medical devices implanted within the body are disclosed. An illustrative method of recharging an implanted medical device includes delivering a charging device to a location adjacent to the implanted medical device, activating a charging element coupled to the charging device and transmitting charging energy to a receiver of the implanted medical device, and charging the implanted medical device using the transmitted charging energy from the charging device.

17 Claims, 12 Drawing Sheets

(56) References Cited

U.S. PATENT DOCUMENTS

| | | |
|---|---|---|
| 4,041,954 A | 8/1977 | Ohara |
| 4,062,354 A | 12/1977 | Taylor et al. |
| 4,082,097 A | 4/1978 | Mann et al. |
| 4,099,530 A | 7/1978 | Chen et al. |
| 4,127,110 A | 11/1978 | Bullara |
| 4,170,742 A | 10/1979 | Itagaki et al. |
| 4,206,761 A | 6/1980 | Cosman |
| 4,206,762 A | 6/1980 | Cosman |
| 4,265,252 A | 5/1981 | Chubbuck et al. |
| 4,281,666 A | 8/1981 | Cosman |
| 4,281,667 A | 8/1981 | Cosman |
| 4,340,038 A | 7/1982 | McKean |
| 4,354,506 A | 10/1982 | Sakaguchi et al. |
| 4,361,153 A | 11/1982 | Slocum et al. |
| 4,378,809 A | 4/1983 | Cosman |
| 4,385,636 A | 5/1983 | Cosman |
| 4,407,296 A | 10/1983 | Anderson |
| 4,471,786 A | 9/1984 | Inagaki et al. |
| 4,481,950 A | 11/1984 | Duggan |
| 4,494,950 A | 1/1985 | Fischell |
| 4,519,401 A | 5/1985 | Ko et al. |
| 4,556,061 A | 12/1985 | Barreras et al. |
| 4,593,703 A | 6/1986 | Cosman |
| 4,596,255 A | 6/1986 | Snell et al. |
| 4,614,192 A | 9/1986 | Imran et al. |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,708,127 A | 11/1987 | Abdelghani |
| 4,719,919 A | 1/1988 | Marchosky et al. |
| 4,791,915 A | 12/1988 | Barsotti et al. |
| 4,791,936 A | 12/1988 | Snell et al. |
| 4,793,825 A | 12/1988 | Benjamin et al. |
| 4,869,251 A | 9/1989 | Lekholm et al. |
| 4,885,002 A | 12/1989 | Watanabe et al. |
| 4,911,217 A | 3/1990 | Dunn et al. |
| 4,918,736 A | 4/1990 | Bordewijk |
| 5,074,310 A | 12/1991 | Mick |
| 5,113,859 A | 5/1992 | Funke |
| 5,117,835 A | 6/1992 | Mick |
| 5,160,870 A | 11/1992 | Carson et al. |
| 5,168,869 A | 12/1992 | Chirife |
| 5,184,605 A | 2/1993 | Grzeszykowski |
| 5,218,861 A | 6/1993 | Brown et al. |
| 5,279,292 A | 1/1994 | Baumann et al. |
| 5,291,899 A | 3/1994 | Watanabe et al. |
| 5,381,067 A | 1/1995 | Greenstein et al. |
| 5,423,334 A | 6/1995 | Jordan |
| 5,433,736 A | 7/1995 | Nilsson |
| 5,445,150 A | 8/1995 | Dumoulin et al. |
| 5,495,453 A | 2/1996 | Wociechowski et al. |
| 5,562,621 A | 10/1996 | Claude et al. |
| 5,619,997 A | 4/1997 | Kaplan |
| 5,620,475 A | 4/1997 | Magnusson |
| 5,704,352 A | 1/1998 | Tremblay et al. |
| 5,704,366 A | 1/1998 | Tacklind et al. |
| 5,712,917 A | 1/1998 | Offutt |
| 5,721,886 A | 2/1998 | Miller |
| 5,724,985 A | 3/1998 | Snell et al. |
| 5,743,267 A | 4/1998 | Nikolic et al. |
| 5,749,909 A | 5/1998 | Schroeppel et al. |
| 5,757,104 A | 5/1998 | Getman et al. |
| 5,759,199 A | 6/1998 | Snell et al. |
| 5,800,478 A | 9/1998 | Chen et al. |
| 5,807,258 A | 9/1998 | Cimochowski et al. |
| 5,814,089 A | 9/1998 | Stokes et al. |
| 5,833,603 A | 11/1998 | Kovacs et al. |
| 5,861,018 A | 1/1999 | Feierbach |
| 5,891,180 A | 4/1999 | Greeninger et al. |
| 5,904,708 A | 5/1999 | Goedeke |
| 5,925,001 A | 7/1999 | Hoyt et al. |
| 5,935,078 A | 8/1999 | Feierbach |
| 5,957,861 A | 9/1999 | Combs et al. |
| 5,967,989 A | 10/1999 | Cimochowski et al. |
| 6,015,387 A | 1/2000 | Schwartz et al. |
| 6,030,374 A | 2/2000 | McDaniel |
| 6,070,103 A | 5/2000 | Ogden |
| 6,140,740 A | 10/2000 | Porat et al. |
| 6,141,588 A | 10/2000 | Cox |
| 6,162,238 A | 12/2000 | Kaplan et al. |
| 6,164,284 A | 12/2000 | Schulman et al. |
| 6,167,303 A | 12/2000 | Thompson |
| 6,170,488 B1 | 1/2001 | Spillman, Jr. et al. |
| 6,176,840 B1 | 1/2001 | Nishimura et al. |
| 6,183,426 B1 | 2/2001 | Akisada et al. |
| 6,185,452 B1 | 2/2001 | Schulman et al. |
| 6,185,454 B1 | 2/2001 | Thompson |
| 6,185,460 B1 | 2/2001 | Thompson |
| 6,198,963 B1 | 3/2001 | Haim et al. |
| 6,198,965 B1 | 3/2001 | Penner et al. |
| 6,198,971 B1 | 3/2001 | Leysieffer |
| 6,200,265 B1 | 3/2001 | Walsh et al. |
| 6,236,889 B1 | 5/2001 | Soykan et al. |
| 6,237,398 B1 | 5/2001 | Porat et al. |
| 6,248,080 B1 | 6/2001 | Miesel et al. |
| 6,259,951 B1 | 7/2001 | Kuzma et al. |
| 6,260,152 B1 | 7/2001 | Cole et al. |
| 6,261,249 B1 | 7/2001 | Tallish et al. |
| 6,277,078 B1 | 8/2001 | Porat et al. |
| 6,315,721 B2 | 11/2001 | Schulman et al. |
| 6,427,088 B1 | 7/2002 | Bowman et al. |
| 6,431,175 B1 | 8/2002 | Penner et al. |
| 6,432,050 B1 | 8/2002 | Porat et al. |
| 6,442,413 B1 | 8/2002 | Silver |
| 6,442,433 B1 | 8/2002 | Linberg |
| 6,472,991 B1 | 10/2002 | Schulman et al. |
| 6,473,638 B2 | 10/2002 | Ferek-Petric |
| 6,564,807 B1 | 5/2003 | Schulman et al. |
| 6,577,899 B2 | 6/2003 | Lebel et al. |
| 6,584,352 B2 | 6/2003 | Combs et al. |
| 6,607,485 B2 | 8/2003 | Bardy |
| 6,628,989 B1 | 9/2003 | Penner et al. |
| 6,644,322 B2 | 11/2003 | Webb |
| 6,664,763 B2 | 12/2003 | Echarri et al. |
| 6,671,552 B2 | 12/2003 | Merritt et al. |
| 6,676,601 B1 | 1/2004 | Lacoste et al. |
| 6,689,091 B2 | 2/2004 | Bui et al. |
| 6,712,772 B2 | 3/2004 | Cohen et al. |
| 6,731,976 B2 | 5/2004 | Penn et al. |
| 6,735,532 B2 | 5/2004 | Freed et al. |
| 6,754,538 B2 | 6/2004 | Linberg |
| 6,764,446 B2 | 7/2004 | Wolinsky et al. |
| 6,788,973 B2 | 9/2004 | Davis et al. |
| 6,790,187 B2 | 9/2004 | Thompson et al. |
| 6,799,280 B1 | 9/2004 | Edenfield et al. |
| 6,804,557 B1 | 10/2004 | Kroll |
| 6,826,430 B2 | 11/2004 | Faltys et al. |
| 6,855,115 B2 | 2/2005 | Fonseca et al. |
| 6,873,869 B2 | 3/2005 | Fischer |
| 6,960,801 B2 | 11/2005 | Lung |
| 6,970,037 B2 | 11/2005 | Sakhuja et al. |
| 6,978,181 B1 | 12/2005 | Snell |
| 6,985,088 B2 | 1/2006 | Goetz et al. |
| 6,985,773 B2 | 1/2006 | Von Arx et al. |
| 6,988,215 B2 | 1/2006 | Splett et al. |
| 6,993,393 B2 | 1/2006 | Von Arx et al. |
| 7,003,349 B1 | 2/2006 | Andersson et al. |
| 7,013,178 B2 | 3/2006 | Reinke et al. |
| 7,024,248 B2 | 4/2006 | Penner et al. |
| 7,027,871 B2 | 4/2006 | Burnes et al. |
| 7,027,872 B2 | 4/2006 | Thompson |
| 7,035,684 B2 | 4/2006 | Lee |
| 7,060,030 B2 | 6/2006 | Von Arx et al. |
| 7,061,381 B2 | 6/2006 | Forcier et al. |
| 7,082,334 B2 | 7/2006 | Boute et al. |
| 7,096,068 B2 | 8/2006 | Mass et al. |
| 7,123,964 B2 | 10/2006 | Betzold et al. |
| 7,198,603 B2 | 4/2007 | Penner et al. |
| 7,203,551 B2 | 4/2007 | Houben et al. |
| 7,209,790 B2 | 4/2007 | Thompson et al. |
| 7,212,133 B2 | 5/2007 | Goetz et al. |

(56) References Cited

U.S. PATENT DOCUMENTS

| | | |
|---|---|---|
| 7,236,821 B2 | 6/2007 | Cates et al. |
| 7,273,457 B2 | 9/2007 | Penner et al. |
| 7,283,874 B2 | 10/2007 | Penner et al. |
| 7,286,872 B2 | 10/2007 | Kramer et al. |
| 7,319,903 B2 | 1/2008 | Bange et al. |
| 7,335,161 B2 | 2/2008 | Von Arx et al. |
| 7,353,063 B2 | 4/2008 | Simms, Jr. |
| 7,469,161 B1 | 12/2008 | Gandhi et al. |
| 7,479,108 B2 | 1/2009 | Rini et al. |
| 7,617,001 B2 | 11/2009 | Penner et al. |
| 7,650,185 B2 | 1/2010 | Maile et al. |
| 7,756,587 B2 | 7/2010 | Penner et al. |
| 8,340,776 B2 | 12/2012 | Doron et al. |
| 2001/0025139 A1 | 9/2001 | Pearlman |
| 2002/0065540 A1 | 5/2002 | Lebel et al. |
| 2002/0077673 A1 | 6/2002 | Penner et al. |
| 2002/0151770 A1 | 10/2002 | Noll, III et al. |
| 2003/0114897 A1 | 6/2003 | Von Arx et al. |
| 2003/0212441 A1 | 11/2003 | Starkweather et al. |
| 2004/0039424 A1 | 2/2004 | Merritt et al. |
| 2004/0133092 A1 | 7/2004 | Kain |
| 2004/0152999 A1 | 8/2004 | Cohen et al. |
| 2004/0172083 A1 | 9/2004 | Penner |
| 2004/0210141 A1 | 10/2004 | Miller |
| 2005/0113705 A1 | 5/2005 | Fischell et al. |
| 2005/0136385 A1 | 6/2005 | Mann et al. |
| 2005/0159785 A1 | 7/2005 | Rueter |
| 2005/0159789 A1 | 7/2005 | Brockway et al. |
| 2005/0177135 A1 | 8/2005 | Hildebrand et al. |
| 2005/0203444 A1 | 9/2005 | Schonenberger et al. |
| 2005/0288727 A1 | 12/2005 | Penner |
| 2006/0009818 A1 | 1/2006 | Von Arx et al. |
| 2006/0020307 A1 | 1/2006 | Davis et al. |
| 2006/0025834 A1 | 2/2006 | Von Arx et al. |
| 2006/0031378 A1 | 2/2006 | Vallapureddy et al. |
| 2006/0041287 A1 | 2/2006 | Dewing et al. |
| 2006/0041288 A1 | 2/2006 | Dewing et al. |
| 2006/0058627 A1 | 3/2006 | Flaherty et al. |
| 2006/0064134 A1 | 3/2006 | Mazar et al. |
| 2006/0064135 A1 | 3/2006 | Brockway |
| 2006/0064142 A1 | 3/2006 | Chavan et al. |
| 2006/0085039 A1 | 4/2006 | Hastings et al. |
| 2006/0122667 A1 | 6/2006 | Chavan et al. |
| 2006/0142819 A1 | 6/2006 | Penner et al. |
| 2006/0149329 A1 | 7/2006 | Penner |
| 2007/0010742 A1 | 1/2007 | Torp et al. |
| 2007/0055313 A1 | 3/2007 | Stahmann et al. |
| 2007/0142728 A1 | 6/2007 | Penner et al. |
| 2007/0150014 A1 | 6/2007 | Kramer et al. |
| 2007/0162090 A1 | 7/2007 | Penner |
| 2007/0179549 A1 | 8/2007 | Russie |
| 2007/0250126 A1 | 10/2007 | Maile et al. |
| 2008/0015421 A1 | 1/2008 | Penner |
| 2008/0071178 A1 | 3/2008 | Greenland et al. |
| 2008/0103553 A1 | 5/2008 | Penner et al. |
| 2008/0108915 A1 | 5/2008 | Penner |
| 2008/0171941 A1 | 7/2008 | Huelskamp et al. |
| 2008/0195002 A1 | 8/2008 | Thompson et al. |
| 2008/0243210 A1 | 10/2008 | Doron et al. |
| 2009/0198295 A1* | 8/2009 | Dennis et al. .................... 607/4 |
| 2009/0312650 A1 | 12/2009 | Maile et al. |
| 2009/0326609 A1 | 12/2009 | Doron |
| 2010/0023091 A1 | 1/2010 | Stahmann et al. |
| 2010/0114215 A1* | 5/2010 | Burnes et al. .................... 607/5 |
| 2011/0071585 A1* | 3/2011 | Ransbury et al. ................ 607/4 |
| 2011/0160804 A1 | 6/2011 | Penner |

FOREIGN PATENT DOCUMENTS

| | | |
|---|---|---|
| EP | 1962557 A2 | 8/2008 |
| JP | 10-505529 | 6/1998 |
| JP | 2002-515807 | 5/2002 |
| JP | 2004-041724 | 2/2004 |
| JP | 2004-511313 | 4/2004 |
| JP | 2004537347 | 12/2004 |
| JP | 2005521528 | 7/2005 |
| WO | WO 88/02250 | 4/1988 |
| WO | WO 9626673 A1 | 9/1996 |
| WO | WO 98/43338 | 10/1998 |
| WO | WO 98/43701 | 10/1998 |
| WO | WO 99/34453 | 7/1999 |
| WO | WO 00/47109 | 8/2000 |
| WO | WO 01/28627 | 4/2001 |
| WO | WO 01/74278 | 10/2001 |
| WO | WO 01-76687 | 10/2001 |
| WO | WO 01/97907 | 12/2001 |
| WO | WO 02/03347 | 1/2002 |
| WO | 0232502 | 4/2002 |
| WO | WO 02089904 A1 | 11/2002 |
| WO | WO 03/002243 | 1/2003 |
| WO | 2003043688 A1 | 5/2003 |
| WO | WO 03/096889 | 11/2003 |
| WO | WO 2004-089465 | 10/2004 |
| WO | WO 2005/009535 | 2/2005 |
| WO | WO 2005/053786 | 6/2005 |
| WO | WO 2005-099816 | 10/2005 |
| WO | WO 2006-017615 | 2/2006 |
| WO | WO 2006-034183 | 3/2006 |
| WO | WO 2006/060668 | 6/2006 |
| WO | WO 2006/126401 | 11/2006 |
| WO | WO 2007/070794 | 6/2007 |
| WO | WO 2007/080487 | 7/2007 |
| WO | WO 2007/127696 | 11/2007 |
| WO | WO 2008/118908 | 10/2008 |
| WO | WO 2010062538 A1 | 6/2010 |

OTHER PUBLICATIONS

IEEE Transactions on Biomedical Engineering, vol. 42, No. 5, May 1995, Title: Data Transmission from an Implantable Biotelemeter by Load-Shift Keying Using Circuit Configuration Modulator, by Zhengnian Tang, Brian Smith, John H. Schild, and P. Hunter Peckham, pp. 524-528.

Ishiwara et al., "Current Status and Prospects of FET-Type Ferroelectric Memories," Journal of Semiconductor Technology and Science 1(1): Mar. 1-14, 2001.

Neurosurgery Clinics of North America vol. 4, No. 4, Oct. 1993, Hydrocephalus, Title: The Treatment of Hydrocephalus by Paul M. Kanev, MD, and T.S. Park, MD., pp. 611-619.

Neurosurgery Clinics of North America, vol. 4, No. 4, Oct. 1993, Hydrocephalus, Title: Complications in Ventricular Cerebrospinal Fluid Shunting by Jeffrey P. Blount, MD, John A. Campbell, MD, and Stephen J. Haines, MD, pp. 633-656.

Neurosurgery Update II Vascular, Spinal, Pediatric, and Functional Neurosurgery, Published by McGraw-Hill, Inc., 1991, Editors Robert H. Wilkins, M.D., and Setti S. Rengachary, M.D., Title Shunt Complications by R. Michael Scott, pp. 300-319.

Neurosurgery, vol. 34, No. 5, May 1994, Concepts and Innovations, Title: A New Ventricular Catheter for the Prevention and Treatment of Proximal Obstruction in Cerebrospinal Fluid Shunts, by Enrique C.G. Ventureyra, M.D., F.R.C.S.(C)., F.A.C.S., Michael J. Higgins, M.D., pp. 924-926.

Neurosurgery, vol. 34, No. 6, Jun. 1994, Rapid Communication, Title: The Use of the Codman-Medos Programmable Hakim Valve in the Management of Patients with Hydrocephalus: Illustrative Cases, by Peter McL. Black, M.D., Ph.D., Rodolfo Hakim, M.D., Nancy Olsen Bailey, R.N., B.S.N., M.B.A., pp. 1110-1113.

Pediatric Neurosurgery 2nd Edition, Surgery of the Developing Nervous System, Published by W.B. Saunders Company Harcourt Brace Jovanovich, Inc., 1989. Title: Treatment of Hydrocephalus by Harold L. Rekate, M.D.; Ventricular Shunts: Complications and Results by Robert L. McLaurin, M.D.; pp. 200-229.

International Search Report and Written Opinion issued in PCT/US2009/062019, mailed Apr. 12, 2010, 14 pages.

\* cited by examiner

METHODS AND SYSTEMS FOR RECHARGING AN IMPLANTED DEVICE BY DELIVERING A SECTION OF A CHARGING DEVICE ADJACENT THE IMPLANTED DEVICE WITHIN A BODY

CROSS-REFERENCE TO RELATED APPLICATION

This application claims priority under 35 U.S.C. § 119 to U.S. Provisional Application No. 61/108,635, filed on Oct. 27, 2008, entitled "Methods and Systems for Recharging Implantable Devices," which is incorporated herein by reference in its entirety for all purposes.

TECHNICAL FIELD

The present invention relates generally to implantable medical devices including rechargeable power sources. More specifically, the present invention pertains to methods, systems, and apparatus for recharging medical devices implanted within the body.

BACKGROUND

Actively powered implantable medical devices sometimes require a power supply such as a battery or power capacitor to provide electrical power to the device, in some cases over an extended period of time. In cardiac rhythm management applications, for example, an implantable medical device such as a pressure sensor may require a power supply capable of operating the device over a period of several years. In some cases, the time required to power the device is beyond the capability of the power supply, requiring replacement of the power supply or the implantation of a new device within the body.

With advances in power management and battery technology, more recent trends have focused on the use of small rechargeable power sources for providing power to implantable devices. Current charging techniques often rely on the patient and/or a health-care provider to ensure that the battery is charged periodically. In some cases, the patient may be required to undergo recharging within a clinical environment, which can be burdensome to the patient and often adds to the overall costs associated with recharging. If recharging is to be performed in a clinic, for example, a special area may be required for the patient while the recharging is being performed, adding to the overall cost and time associated with the maintenance.

SUMMARY

The present invention pertains to methods, systems, and apparatus for recharging medical devices implanted within the body. An illustrative recharging system includes a device implanted within a body lumen having a rechargeable power source and a receiver, and a charging device adapted to provide charging energy to the implanted device from a location within the body adjacent to the device. A charging element coupled to the charging device is configured to transmit energy at a location within the body proximate to the receiver. In some embodiments, for example, the charging element includes a source transducer adapted to transmit an acoustic signal to a target transducer coupled to the implanted device for acoustically recharging the device. Alternatively, and in other embodiments, the charging element includes an electromagnetic transmitter adapted to transmit an electromagnetic signal to an antenna or coil coupled to the implanted device for recharging the device using RF or other forms of electromagnetic energy. Other energy transfer modes can also be employed for recharging the implanted device.

An illustrative method of recharging a medical device implanted within a body lumen of a patient's body includes delivering a distal section of the charging device to a location adjacent to the implanted device, activating a charging element operatively coupled to a power source and wirelessly transmitting energy to a receiver coupled to the implanted device, and converting the energy received by the receiver into electrical energy for charging the implanted device. The charging device can be positioned at a target location within the same body lumen as the implanted device, or alternatively, within a different body lumen. For recharging a pressure sensor implanted within a pulmonary artery, for example, the charging device can be delivered to a location within the pulmonary artery, an adjacent artery, or an adjacent lumen or cavity such as the aorta or esophagus. Once positioned adjacent to the implanted device, the charging element can be activated to transmit charging energy to the device from a position within the body. In some embodiments, the charging device can be used to perform other functions within the body such as calibrating the implanted device, confirming the proper operation of the charging device, and/or performing therapy within the body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
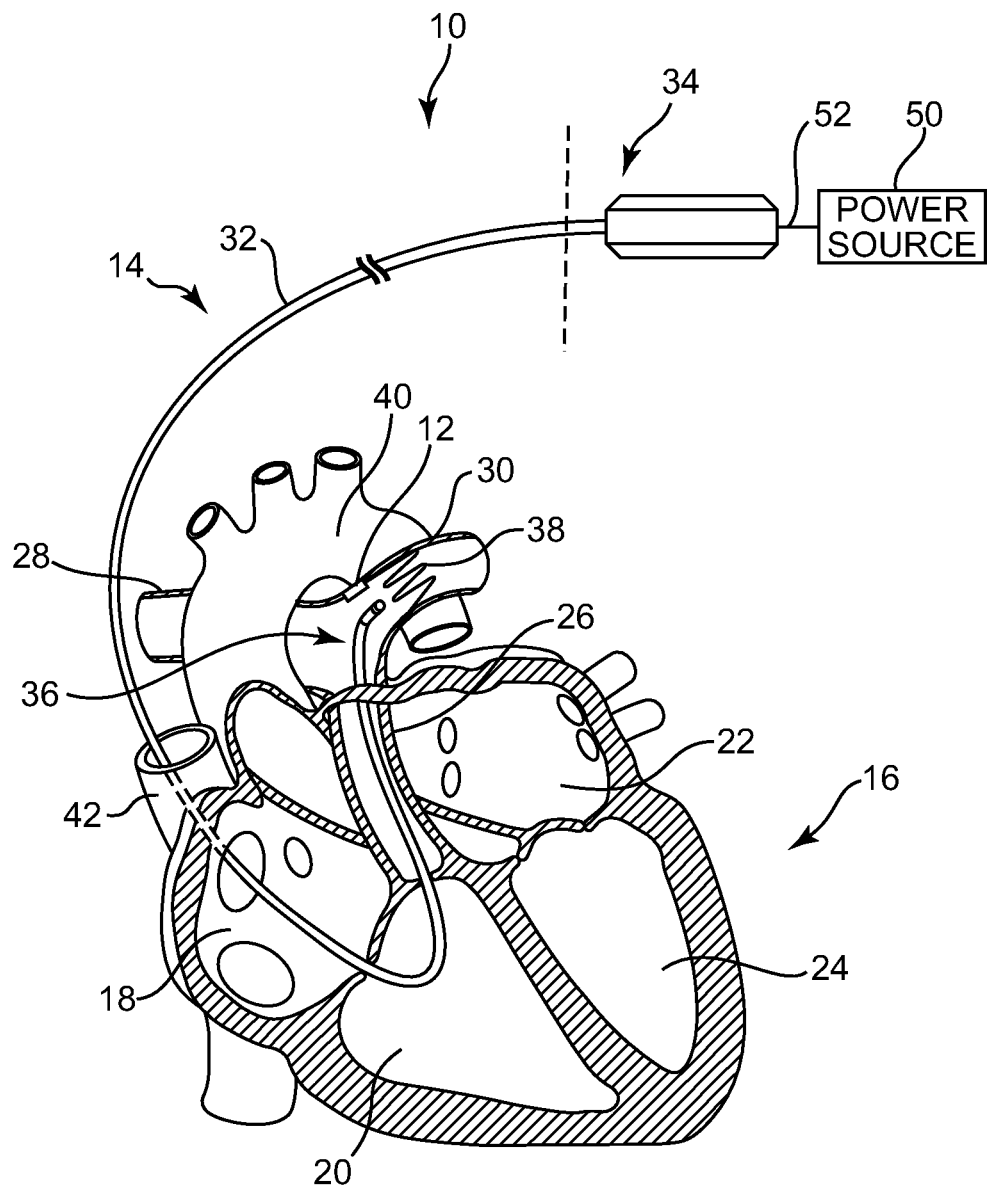
FIG. 1 is a schematic view of an illustrative system for recharging a medical device implanted within a body lumen.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an illustrative system 10 for recharging a medical device implanted within a body lumen. The system 10, illustratively a system for recharging a device 12 implanted within a pulmonary artery, includes a charging catheter 14 adapted for insertion at a target location within a patient's body such as in or near the heart 16. The heart 16 includes a right atrium 18, a right ventricle 20, a left atrium 22, and a left ventricle 24. The right ventricle 20 leads to the main pulmonary artery 26, which further branches to the right pulmonary artery 28 and the left pulmonary artery 30, as shown.

The charging catheter 14 includes an elongate shaft 32 having a proximal section 34 located outside of the patient's body, and a distal section 36 insertable into the patient's body at a location adjacent to the implanted device 12. In the illustrative embodiment of FIG. 1, the distal section 36 of the elongate shaft 32 is shown inserted into the main pulmonary artery 26 of the heart 16 at a location adjacent to the device 12, which is shown secured within a portion of the left pulmonary artery 30 via a fixation element 38. The distal section 36 of the charging catheter 14 can be positioned at other locations within the body, including the right pulmonary artery 28, the left pulmonary artery 30, or an adjacent vessel or body lumen such as the aorta 40, as discussed further herein. The positioning of the charging catheter 14 within the body will typically depend on the implantation location and configuration of the implanted device 12 to be recharged, the anatomy surrounding the implanted device 12, as well as other factors.

In some embodiments, the charging catheter 14 can be inserted into the main pulmonary artery 26 via an intravenous approach from a percutaneous access site such as a femoral artery or jugular vein. As shown in FIG. 1, for example, delivery of the charging catheter 14 to a target location within the body can occur intravenously through the superior vena cava 42, the right atrium 18, the right ventricle 20, and the main pulmonary artery 26. Other techniques for inserting the charging catheter 14 into the right pulmonary artery 26 are also possible. In some alternative embodiments, for example, the charging catheter 14 can be inserted into the main pulmonary artery 26 via an intra-arterial approach, percutaneously without the aid of vascular conduits, or via the esophagus, airway, or other conduit.

The implanted device 12 can be configured to perform one or more designated functions, including the sensing of physiological parameters within the body and/or providing therapy to the patient. Example physiological parameters that can be sensed using the implanted device 12 include, but are not limited to, blood pressure, blood or fluid flow, temperature, and strain. Various electrical, chemical, and/or magnetic properties may also be sensed within the body using the implanted device 12. The specific configuration and function to be performed by the implanted device 12 will typically vary depending on the particular therapeutic needs of the patient.

In some embodiments, the implanted device 12 comprises a pressure sensor adapted to sense arterial blood pressure within a pulmonary artery. As shown in the illustrative system 10 of FIG. 1, for example, the implanted device 12 may comprise a pressure sensor implanted in the left pulmonary artery 30 for sensing arterial blood pressure. Alternatively, and in other embodiments, the device 12 may be implanted in the right pulmonary artery 28, the main pulmonary artery 26, or in another vessel leading into or from the heart 16. The implanted device 12 can also be implanted at other locations within the heart 16 such as in the right atrium 18, the right ventricle 20, the left atrium 22, or the left ventricle 24. In some embodiments, the implanted device 12 can be placed at other locations in the body such as within an organ such as the liver or kidney, the vasculature, muscle tissue, or an airway within the body.

The implanted device 12 can be used as part of a cardiac rhythm management (CRM) system to predict decompensation of a heart failure patient, to optimize pacing and/or defibrillation therapy, as well as perform other designated functions within the body. In certain embodiments, for example, the implanted device 12 can be configured to transmit sensed physiological parameters to other CRM system components located within the body such as a pacemaker or defibrillator. In some embodiments, the implanted device 12 can be configured to transmit sensed physiological parameters to an external device such as a monitor or programmer for further monitoring and/or processing. Based on this information, an indication of any abnormalities within the heart 16 can be determined and an appropriate therapy provided to the patient, as necessary.

Figure 2:
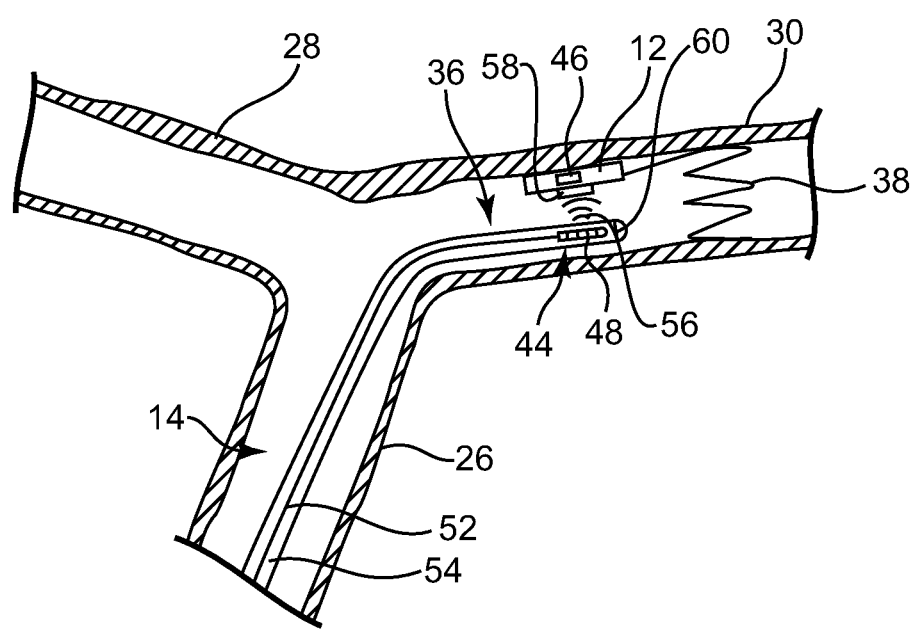
FIG. 2 is a partial cross-sectional view showing the distal section of the charging device of FIG. 1 inserted at a target location within the body adjacent to the implanted device.

FIG. 2 is a partial cross-sectional view showing the distal section 36 of the charging catheter 14 of FIG. 1 inserted at a target location within the body adjacent to the implanted device 12. As can be further seen in FIG. 2, and in some embodiments, the distal section 36 of the charging catheter 14 includes a charging element 44 adapted to transmit energy to the implanted device 12 that can be used to charge a rechargeable battery 46 within the device 12. In certain embodiments, for example, the charging element 44 includes an ultrasonic transducer 48 electrically coupled to an external power source 50 via a number of wires 52 extending through an interior lumen 54 of the charging catheter 14. An example piezoelectric transducer that can be used for acoustically transmitting charging energy to the implanted device 12 is described, for example, in U.S. Pat. No. 6,140,740, entitled "Piezoelectric Transducer," which is incorporated herein by reference in its entirety. Other types of acoustic transducers can also be utilized for providing charging energy to the implanted device 12. In some embodiments, the ultrasonic transducer 48 includes an array of ultrasonic elements.

During recharging, the power source 50 can be configured to deliver a time-varying excitation current to the ultrasonic transducer 48, causing the transducer 48 to generate an acoustic signal 56 within the body that is received by a receiver 58 coupled to the implanted device 12. In some embodiments, for example, the receiver 58 comprises an ultrasonic transducer sensitive to the frequency of the acoustic signal 56 transmitted from the source ultrasonic transducer 48. The acoustic signal 56 received by the target ultrasonic transducer 58 is then converted into electrical energy that can be used to recharge the battery 46.

During delivery, the source ultrasonic transducer 48 on the charging catheter 14 can be positioned in close proximity to the target ultrasonic transducer 58 of the implanted device 12.

In certain embodiments, for example, the distal section 36 of the charging catheter 14 can be positioned such that the source ultrasonic transducer 48 is located a distance of between about 1 mm to about 10 mm apart from the target ultrasonic transducer 58. The distance at which the two transducers 48,58 are spaced apart from each other may be greater or lesser, however, depending on the type of transducers 48,58 employed, the intensity and frequency characteristics of the acoustic signal 56 transmitted, the anatomy surrounding the transducers 48,58, as well as other factors. In some embodiments, the positioning of the charging catheter 14 can be accomplished under the aid of fluoroscopy. A radiopaque marker band 60 placed at or near the distal end of the charging catheter 14 can be used in conjunction with a fluoroscope to visualize the location of the charging catheter 14 during delivery so as to minimize the distance between the transducers 48,58.

Once the distal section 36 of the charging catheter 14 is positioned at a target location within the body adjacent to the implanted device 12, the ultrasonic transducer 48 can be activated to transmit an acoustic signal 56 to the implanted device 12 for recharging the battery 46 in vivo. The time required to deliver a sufficient amount of charging energy to recharge the battery 46 may be affected by several factors, including the location of the device 12 within the body, the location of the charging catheter 14 within the body, the distance between the source and target ultrasonic transducers 48,58, and the intensity and frequency of the acoustic signal 56. Typically, the acoustic intensity of the acoustic signal 56 falls off inversely proportional to the square of the distance from the ultrasonic transducer 48. Thus, for a given flux of energy, there is an initial rapid decrease in intensity in the near field followed by a more gradual decline further away from the transducer 48.

By placing the source and target transducers 48,58 in close proximity to each other, the attenuation loss associated with the rapid fall off of acoustic energy in the near field is reduced, resulting in an increase in charge coupling efficiency. This increase in efficiency reduces the overall time required to recharge the battery 46, and subjects the body to less energy than would otherwise be required to recharge the battery 46 via an external recharging approach with the source ultrasonic transducer transmitting the charging energy directly into the body. This results in a higher intensity field in the vicinity of the implanted device 12 while maintaining a lower overall energy flux transmitted into the body. In addition, because the source transducer 48 is located in close proximity to the target transducer 58, a smaller portion of the transmitted acoustic energy is absorbed and/or scattered within the body, resulting in more efficient charging with reduced body tissue and fluid heating.

Although the illustrative charging catheter 14 of FIG. 2 includes an ultrasonic transducer 48 for acoustically recharging the implanted device 12, in other embodiments the charging element 44 can use other energy transfer modes for transmitting charging energy to the device 12. Examples of other types of energy transfer modes can include, but are not limited to, inductive, electromagnetic, RF, optical (e.g., infrared light, visible light, ultraviolet light, and X-ray), vibration (e.g., transverse and longitudinal mechanical vibrations), radioactive energy, heat, and/or pressure. In one alternative embodiment, for example, the charging element 44 comprises a transmitter adapted to transmit electromagnetic energy to the implanted device 12. The electromagnetic energy transmitted by the charging element 44 is received by an antenna or coil coupled to the implanted device 12, which is then converted into electrical energy for recharging the battery 46. As with an acoustic energy transfer mode, the transmitter can be positioned in close proximity to the antenna or coil in order to reduce attenuation and absorption of the transmitted electromagnetic energy. In certain embodiments, for example, the charging catheter 14 can be positioned such that the charging element 44 is located a distance of between about 1 mm to about 10 mm apart from the antenna or coil for the implanted device 12.

In some embodiments, the charging catheter 14 further includes a focusing or collimating element adapted to direct and focus the charging energy transmitted to the implanted device 12. In those embodiments in which the charging element 44 includes an ultrasonic transducer 48, for example, the charging element 44 may further include an acoustic baffle or lens for focusing the acoustic signal 56 in the direction of the target transducer 58. In some embodiments, focusing of the acoustic signal 56 may occur by selectively activating one or more ultrasonic transducer elements within a transducer array, by adjusting the timing or phase of one or more ultrasonic transducer elements, and/or by adjusting the intensity levels of one or more ultrasonic transducer elements. Other techniques for focusing the transmitted acoustic signal 56 are also possible.

In certain embodiments, the charging element 44 is configured to provide charging energy to the implanted device 12 by directly contacting a surface on the device 12. In one such embodiment, for example, the charging element 44 includes an electrode adapted to electrically contact a corresponding electrode on the implanted device 12. During delivery, the distal section 36 of the charging catheter 14 can be positioned within the body such that the two electrodes make electrical contact with each other. Once positioned, the electrode on the charging catheter 14 can be energized, causing current to flow to the electrode on the implanted device 12. As with other energy transmission modes discussed herein, the charging energy received by the implanted device 12 can then be used to recharge the battery 46.

Figure 3:
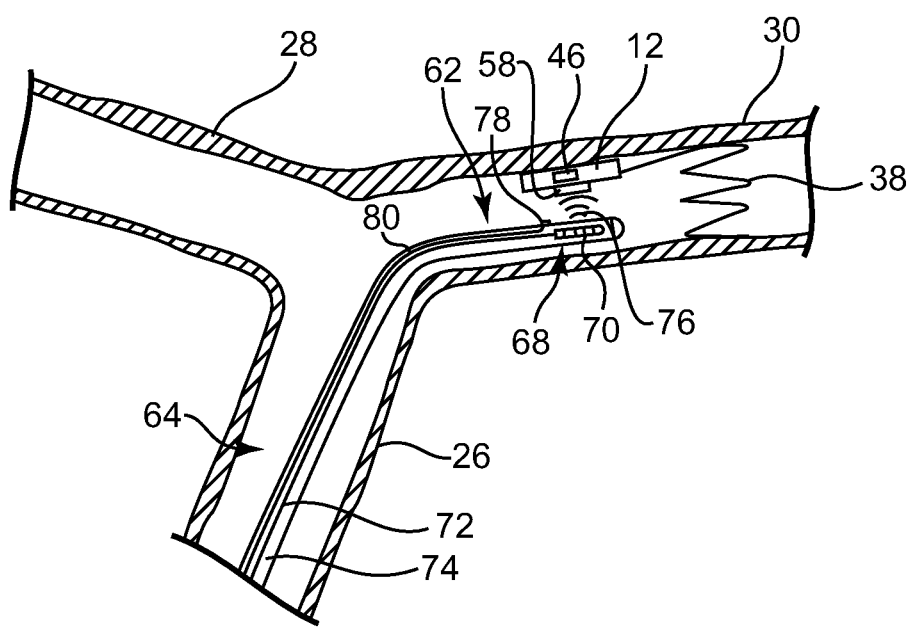
FIG. 3 is a partial cross-sectional view showing the distal section of a charging device in accordance with another illustrative embodiment including a sensor.

FIG. 3 is a partial cross-sectional view showing the distal section 62 of a charging catheter 64 in accordance with another illustrative embodiment including a sensor. As shown in FIG. 3, the distal section 62 of the charging catheter 64 includes a charging element 68 adapted to transmit energy to the implanted device 12, which can be used to charge a rechargeable battery 46 within the device 12. In certain embodiments, for example, the charging element 68 includes an ultrasonic transducer 70, or alternatively, multiple ultrasonic transducers 70 each electrically coupled to an external power source via a number of wires 72 extending through an interior lumen 74 of the charging catheter 64. In use, the ultrasonic transducer(s) 70 can be activated to transmit an acoustic signal 76 to the implanted device 12 for recharging the battery 46 in vivo in a manner similar to that described above with respect to the charging catheter 14 of FIG. 2.

In some embodiments, and as further shown in FIG. 3, the distal section 62 of the charging catheter 64 further includes at least one sensor 78 electrically coupled to the power source 50 via a wire 80 and adapted to monitor one or more parameters associated with the operation of the charging catheter 64 and/or the surrounding environment. Example parameters related to the operation of the charging catheter 64 that can be monitored can include, but are not limited to, parameters related to the energy transmitted by the ultrasonic transducer(s) 70 such as peak power, average power, or power gradient. Example parameters related to the surrounding environment that can be monitored can include, but are not limited to, temperature, electrical impedance, electrical potential, dielectric coefficient, and/or changes in one or more of these parameters. The sensor 78 can also be configured to sensor other parameters associated with the operation of the charging catheter, the implanted device 12, and/or the surrounding environment.

In certain embodiments, the sensor 78 is a temperature sensor 78 adapted to measure the temperature of body tissue and/or the local blood temperature at or near the location of the implanted device 12. In some embodiments, for example, the temperature sensor 78 can be configured to sense the local blood temperature of blood in the path of the acoustic signal 76, which can be used to estimate the temperature of the body tissue adjacent to the implanted device 12. The charging catheter 64 can be positioned within the vessel such that the temperature sensor 78 contacts the body tissue within the vessel, allowing the sensor 78 to directly sense the body tissue temperature adjacent to the implanted device 12. Based on the monitored temperature, the system can then either reduce the power of the acoustic energy transmitted by the ultrasonic transducer(s) 70, or alternatively, disable one or more of the transducers 70 in the event the temperature exceeds a maximum temperature threshold value. The monitored temperature can also be provided as feedback to notify a clinician of a potentially hazardous condition related to the operation of the charging catheter 64. The temperature sensor 78 can also be utilized to perform other tasks such as calibrating the charging element 68.

In some embodiments, the sensor 78 can be configured to monitor for the presence of any electrical leakage from the charging element 68. For example, the sensor 78 can comprise a sensor adapted to detect the presence of any current leakage from the ultrasonic transducer(s) 70 into the surround anatomy. The monitoring of electrical leakage from the ultrasonic transducers 70 can be accomplished, for example, by measuring the current into and out of the transducers 70 using a differential current transformer, a bridge circuit, or the like. If an electrical leakage is detected, and depending on its magnitude, the system can then either adjust the operating power provided to one or more of the ultrasonic transducers 70 or disable the transducers 70 in order to reduce or eliminate the electrical leakage. This may be useful, for example, in acoustic charging systems that deliver relatively high voltages to the transducer elements. The charging system can also be configured to notify the clinician if a fault condition has occurred in the charging catheter 64.

The implanted device 12 can be further configured to monitor a number of parameters associated with the acoustic signal 76 received from the charging catheter 64. For example, in those embodiments in which the implanted device 12 includes an energy exchanger (e.g., an ultrasonic transducer), the implanted device 12 can be configured to monitor the power or intensity of the acoustic signal 76 transmitted by the charging catheter 64 to determine whether the signal 76 is within an acceptable range. If the received acoustic signal 76 exceeds a maximum power or intensity value, for example, the implanted device 12 can be configured to communicate a signal back to the charging catheter 64, which can be used by the catheter 64 as feedback to adjust the intensity or power of the signal 76. In some embodiments, the feedback signal can also be used by the clinician to aid in repositioning the charging catheter 64 within the vessel to maximize the charge coupling efficiency between the catheter 64 and the implanted device 12. In one embodiment, for example, the feedback signal can be used to adjust the placement location of charging catheter 64, and in particular the location of the charging element 68 within the vessel, in order to optimize the charging energy received by the implanted device 12.

Figure 4:
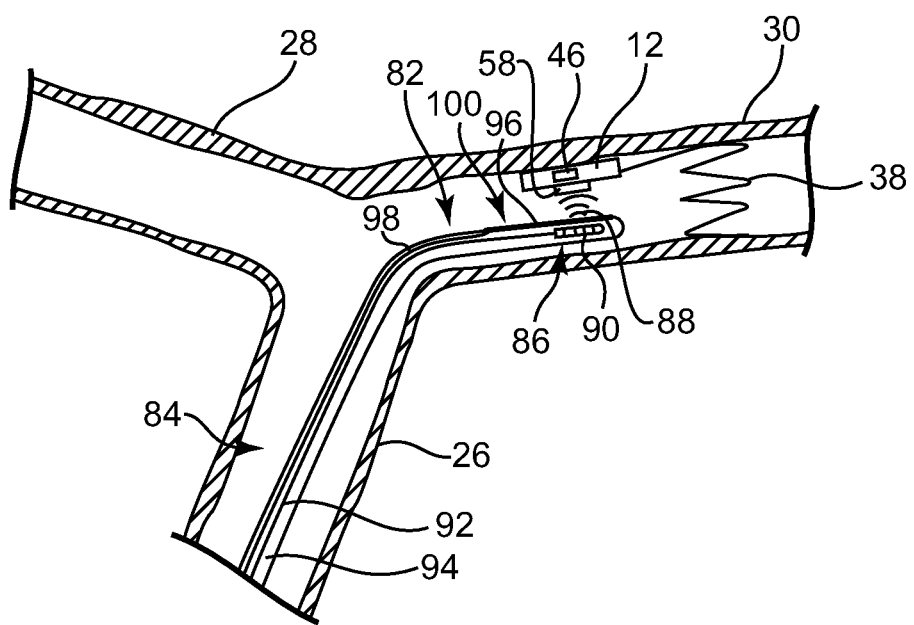
FIG. 4 is a partial cross-sectional view showing the distal section of a charging device in accordance with another illustrative embodiment including a thermocouple wire.

FIG. 4 is a partial cross-sectional view showing the distal section 82 of charging catheter 84 in accordance with another illustrative embodiment including a thermocouple wire for sensing temperature. As shown in FIG. 4, the distal section 82 of the charging catheter 84 includes a charging element 86 adapted to transmit a signal 88 to the implanted device 12. In certain embodiments, the charging element 86 includes an ultrasonic transducer 90, or alternatively, multiple ultrasonic transducers 90 each electrically coupled to an external power source via a number of wires 92 extending through an interior lumen 94 of the charging catheter 84.

In some embodiments, and as further shown in FIG. 4, the charging catheter 84 includes a thermocouple wire 96 adapted to sense the temperature of the body tissue and/or local blood temperature within the vessel at or near the location of the implanted device 12. The thermocouple wire 96 can be embedded within the charging catheter 84 at a location at or near the charging element 86, and can be electrically coupled to sensing electronics within the external power source 50 via a wire 98. The thermocouple wire 96 can be fabricated from a relatively thin gauge metal capable of sensing relatively small changes in temperature. In some embodiments, the sensing electronics can comprise a differential amplifier adapted to convert sensed thermal potential differences into an electrical potential difference indicative of a change in temperature due to the transmitted charging energy.

In use, the thermocouple wire 94 can be configured to sense temperature at the distal section 82 of the charging catheter 84, which can then be used to estimate the temperature of the body tissue and/or blood in the path of the acoustic signal 88. In some embodiments, an exposed portion 100 of the thermocouple wire 96 may permit the wire 96 to sense the local temperature within the blood vessel or, if placed into contact with the vessel wall, the body tissue temperature. The exposed portion 100 of the thermocouple wire 96 can also be used to sense other parameters within the vessel. In certain embodiments, for example, the exposed portion 100 of the thermocouple wire 96 may also function as a voltimeter probe to detect the presence of any electrical leakage from the charging element 86 by measuring electrical potentials within the vessel.

In another embodiment, the thermocouple wire 96 can be coupled directly to the charging element 86 for monitoring the temperature of the element 86 itself. For an acoustic recharging system including an ultrasonic transducer 90, for example, the thermocouple wire 96 can be attached to a portion of the transducer 90 to monitor the temperature of the transducer 90 during recharging. Since heating in the vessel is due in part to heat conduction from the ultrasonic transducer 90, the temperature within the vessel can be monitored indirectly using the thermocouple wire 96. The sensed temperature on the ultrasonic transducer 70 can then be used as feedback for regulating the operating power provided to the transducer 70.

Figure 5:
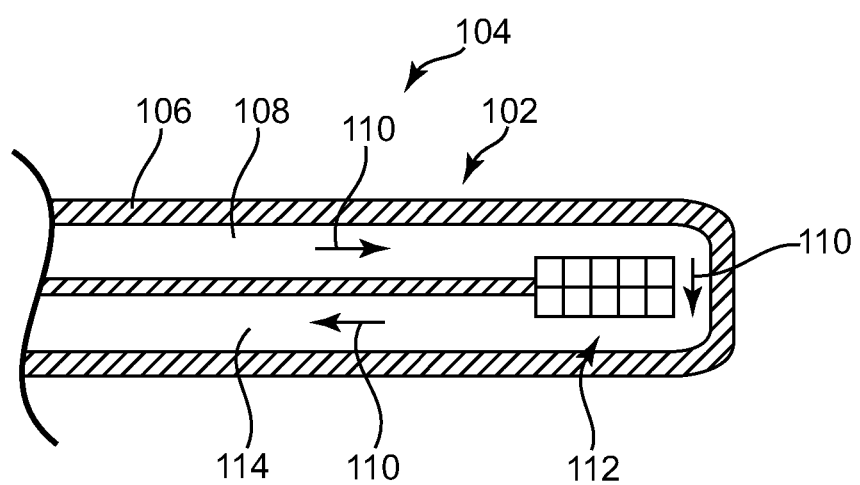
FIG. 5 is a partial cross-sectional view showing the distal section of a charging device in accordance with another illustrative embodiment including a cooling lumen.

FIG. 5 is a partial cross-sectional view showing the distal section 102 of a charging catheter 104 in accordance with another illustrative embodiment including a cooling lumen. As shown in FIG. 5, the charging catheter 104 includes an elongate shaft 106 having an internal lumen 108 in fluid communication with a cooling medium 110 that can be used for cooling a charging element 112 and/or the body tissue and fluids surrounding the distal section 102 of the catheter 104. The cooling medium 110 may comprise a liquid or gas delivered to the distal section 102 of the charging catheter 104 from a source operatively coupled to the proximal section of the catheter 104. In some embodiments, the cooling medium 110 can be configured to change its aggregation state from a liquid to gas when heated. In certain embodiments, for example, the cooling medium 110 comprises a pressurized source of liquid nitrogen operatively coupled to the charging catheter 104 at a location external to the body. Upon heating from the charging element 112, the liquid nitrogen can be configured to change from an initial liquid state to a gaseous state, absorbing heat produced by activation of the element 112 during recharging. Examples of other suitable cooling mediums 110 can include, but are not limited to, air, carbon dioxide, helium, neon, argon, saline, water, or a Freon-based solution.

In some embodiments, an additional lumen 114 can be used as a return line to return the cooling medium 110 back to the proximal section of the charging catheter 104 once heated. During recharging, the cooling medium 110 can be circulated through the interior of the distal section 102 to dissipate the heat generated by the charging element 112 and to reduce heating of the body tissue and fluids surrounding the catheter 104. In some embodiments, the temperature of the cooling medium 110 can be reduced to a temperature below room temperature to further aid in dissipating heat generated by the charging element 112.

During recharging, the presence of the cooling medium 110 within the lumens 108,114 facilitates operation of the charging element 112 at higher intensity levels without causing significant heating in the surrounding body tissue and fluids. When the charging catheter 104 is implanted in a pulmonary artery, for example, the presence of the cooling medium 110 facilitates operation of the charging element 112 at greater intensity levels without heating the blood within the artery. The ability to operate at higher intensity levels without heating may reduce the overall time required to recharge the battery within the implanted device.

Figure 6:
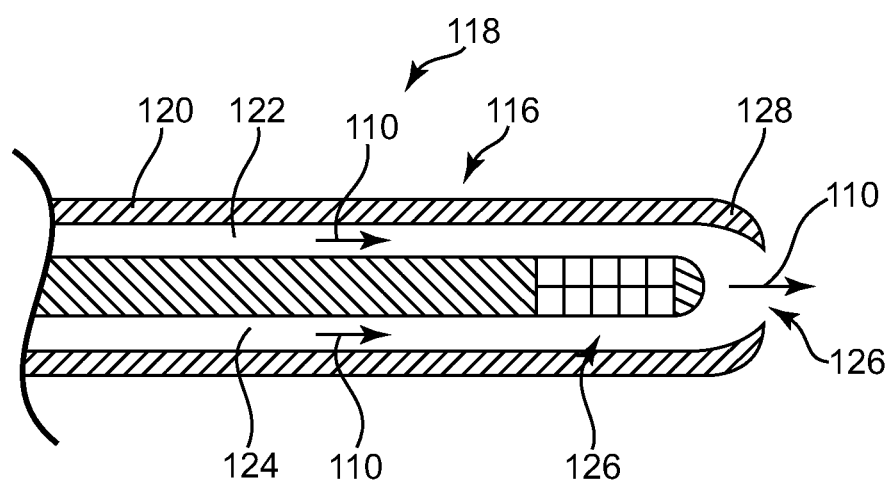
FIG. 6 is a partial cross-sectional view showing the distal section of a charging device in accordance with another illustrative embodiment including a cooling lumen.

FIG. 6 is a partial cross-sectional view showing the distal section 116 of a charging catheter 118 in accordance with another illustrative embodiment including a cooling lumen. Similar to the embodiment of FIG. 5, the charging catheter 118 includes an elongate shaft 120 having one or more internal lumens 122,124 in fluid communication with a cooling medium 110 that can be used for cooling a charging element 126 and/or body tissue and fluids surrounding the distal section 116 of the catheter 118. In the embodiment of FIG. 6, the lumens 122,124 terminate distally at an exit port 126 disposed at or near the distal end 128 of the charging catheter 118. In some embodiments, multiple exit ports may be provided at or near the distal end 128 of the elongate shaft 120 and/or may be provided at various other locations along the length of the shaft 120.

During recharging, a pressurized cooling medium 110 (e.g., saline) contained within the lumens 122,124 is ejected through the port 126 and into the surrounding anatomy. In recharging applications where the catheter 118 is positioned in a pulmonary artery adjacent to an implanted pressure sensor, for example, the cooling medium 110 may be ejected through the exit port 126 and into the artery for cooling the blood within the artery as well as the pressure sensor. As with the embodiment of FIG. 5, the passage of the cooling medium 110 through the lumens 122,124 further dissipates heat generated by the charging element 126.

Figure 7:
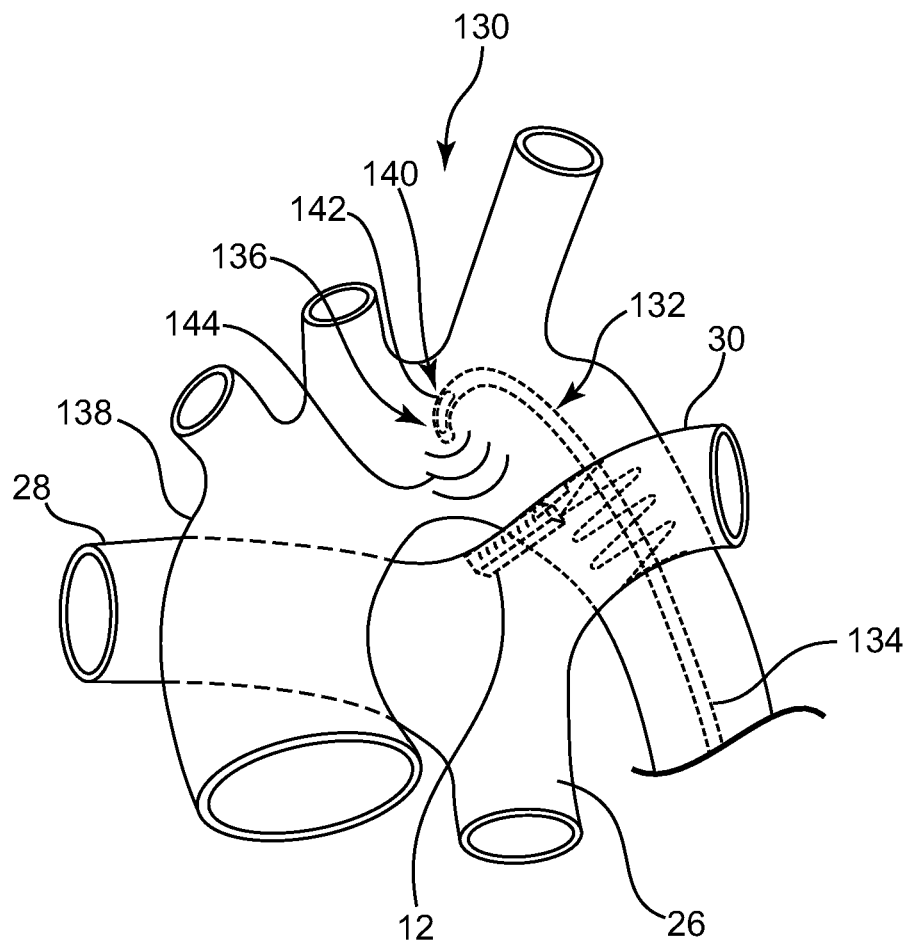
FIG. 7 is a schematic view showing another illustrative system for recharging a medical device implanted within a body lumen.

FIG. 7 is a schematic view of another illustrative system 130 for recharging a medical device 12 implanted within a body lumen. In the illustrative embodiment of FIG. 7, a charging catheter 132 including an elongate shaft 134 having a proximal section (not shown) and a distal section 136 is inserted into a different body vessel in close proximity to the vessel containing the implanted device 12. In an implantable pressure sensor disposed within a pulmonary artery, for example, the distal section 136 of the charging catheter 132 may be positioned within an adjacent body vessel such as the aorta 138. Delivery of the charging catheter 132 to the aorta 138 can be accomplished, for example, via a catheterization approach through a coronary artery. Other delivery techniques, however, are possible.

By positioning the charging catheter 132 into a different vessel than the implanted device 12, access to a target site for recharging may be easier and/or may be less invasive than inserting the catheter 132 directly into the same vessel as the device 12. In some cases, for example, the implanted device 12 may be implanted within a body lumen that is difficult to access. In such case, delivery of the charging catheter 132 to a different vessel within the body (e.g., the aorta, the right pulmonary artery, the esophagus, etc.) may reduce the overall time and difficulty associated with the recharging process.

Once the charging catheter 132 is positioned at a target location within an adjacent body lumen (e.g., the aorta 138), a charging element 140 coupled to the catheter 132 can be activated to transmit charging energy into the adjacent vessel (e.g., the left pulmonary artery 30) for recharging the implanted device 12. In those embodiments in which the charging element 140 includes an ultrasonic transducer 142, for example, the transducer 142 can be configured to transmit an acoustic signal 144 that can be received by the implanted device 12 and converted into electrical energy for recharging the device 12.

In some embodiments, the charging catheter 132 can be used to perform other functions within the body and/or to provide therapy to the patient. In certain embodiments, for example, the charging catheter 132 may be used during a diagnostic or therapeutic coronary artery catheterization (e.g., a right heart catheterization) for treating coronary artery disease within the body. In one such embodiment, the charging element 140 may be provided as part of a coronary balloon catheter for performing an angioplasty procedure on the patient. In such case, recharging of the implanted device 12 may be performed in conjunction with the therapy using the same catheterization.

Figure 8:
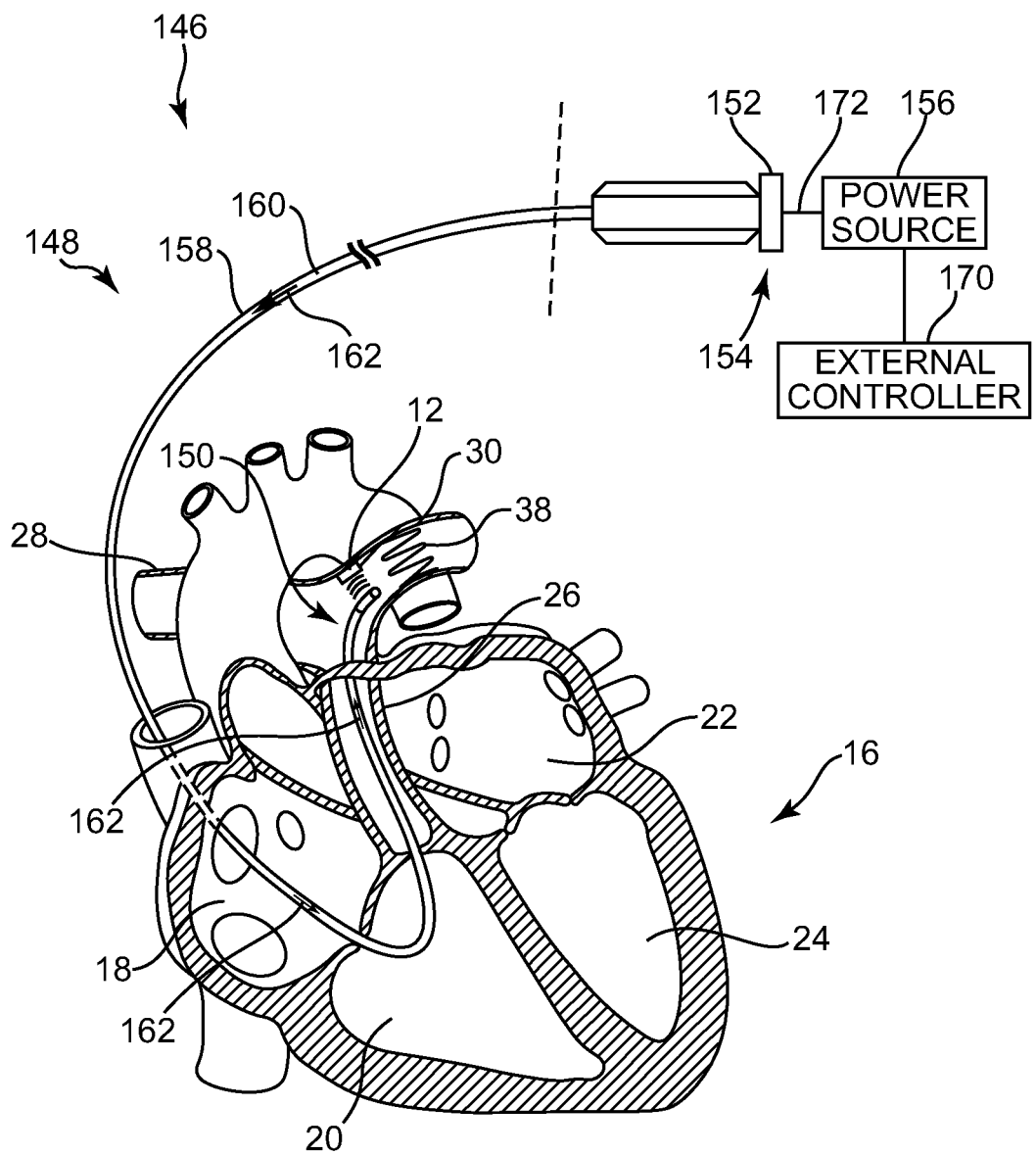
FIG. 8 is a schematic view showing another illustrative system for recharging a medical device implanted within a body lumen.

FIG. 8 is a schematic view showing another illustrative system 146 for recharging a medical device 12 implanted within a body lumen. The system 146, illustratively a system for recharging a pressure sensor implanted within a pulmonary artery, includes a charging catheter 148 having a distal section 150 inserted at a target location within the patient's body, an external charging element 152 coupled to a proximal section 154 of the charging catheter 148, and a power source 156.

The charging catheter 148 includes an elongate shaft 158 having an interior lumen 160 adapted to transmit charging energy generated by the charging element 152 from a location outside of the patient to the distal section 150 of the charging catheter 148. In some embodiments, for example, the charging element 152 comprises an external ultrasonic transducer that, when energized by the power source 156, generates an acoustic signal 162 that is transmitted through the interior lumen 160 to the distal section 150 of the catheter 148. In some embodiments, the ultrasonic transducer 152 comprises an array of ultrasonic transducer elements each of which can be selectively actuated to generate the acoustic signal 162. During recharging, the interior lumen 160 acts as an acoustic waveguide for the acoustic signal 162, reducing attenuation and scattering that would normally occur during transmission of the signal 162 directly through the body. Because the charging element 152 is located outside of the patient's body, the transducer 152 can be of any size and power without significantly impacting the acoustic energy transmitted into the body.

Figure 9:
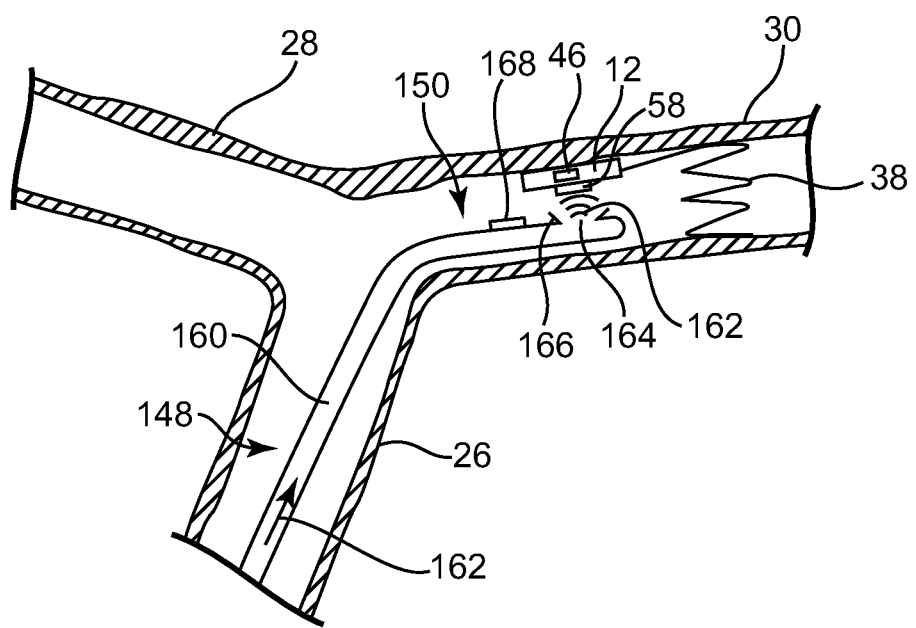
FIG. 9 is a partial cross-sectional view showing the distal section of the charging device of FIG. 8 inserted at a target location within the body adjacent to the implanted device.

FIG. 9 is a partial cross-sectional view showing the distal section 150 of the charging catheter 148 of FIG. 8 inserted at a target location within the body adjacent to an implanted device 12. As can be further seen in FIG. 9, the distal section 150 of the charging catheter 148 includes a port 164 adapted to direct the acoustic signal 162 transmitted through the interior lumen 118 in a direction towards the implanted device 12. In some embodiments, the interior lumen 160 may contain a liquid or solid material (e.g., saline), which acts as an interface to facilitate transmission of the acoustic energy through the interior lumen 160. In certain embodiments, the distal section 150 of the charging catheter 148 may further include a focusing or collimating element 166 such as an acoustic baffle or lens to further focus the acoustic signal 162 in a direction towards the implanted device 12.

In some embodiments, the charging catheter 148 may include other components for use in focusing the charging energy generated by the charging element 152, either passively or actively. In the embodiment of FIG. 9, for example, the charging catheter 148 includes a sensor 168 adapted to sense various parameters of the acoustic signal 162 as it is transmitted from the port 164 towards the implanted device 12. In one embodiment, the sensor 168 is an ultrasonic pressure sensor adapted to sense the intensity and/or phase of the acoustic signal 162 as it exits the port 164. The sensor 168 can be configured to relay pressure sensor readings to an external controller 170 via a wired or wireless communications link. Based on the sensor readings, the external controller 170 can be configured to run an adaptive algorithm or routine that is used to optimize the direction, focusing, phase, intensity, timing, and/or bandwidth of the acoustic signal 162 generated by the charging element 152. In some embodiments, for example, the sensor readings can be used to analyze the intensity and phase of the acoustic signal 162 exiting the port 164, and responsive to these parameters, adjust the intensity and timing of the electrical signal 172 provided to one or more transducer elements of the charging element 152, either simultaneously or sequentially.

Alternatively, and in other embodiments, the distal section 150 of the charging catheter 148 may include a passive element such as a reflector or an active element such as a repeater adapted to generate a signal 172 that is received by an array of transducer elements. In certain embodiments, for example, the reflected or repeated signal may serve as a reference signal for a time-reversal acoustic algorithm that can be used to generate time reversals on one or more of the transducer elements in order to focus the acoustic signal 162 towards the implanted device 12. The sensor 168 on the charging catheter 148 can be configured to sense an acoustic signal transmitted by the implanted device 12. The sensed acoustic signal can then be transmitted to the external controller 170 for computing phase delays for each of the transducer elements. The external controller 170 can then adjust one or more parameters associated with the ultrasonic elements to focus or steer the acoustic signal 162 towards the implanted device 12. Example parameters that can be adjusted include, but are not limited to, direction, focusing, phase, intensity, timing, and/or bandwidth.

The sensor 168 can be used to perform other functions within the body such as calibrating the implanted device 12. In those embodiments in which the implanted device 12 comprises a pressure sensor, for example, the sensor 168 may be used as a reference pressure sensor to calibrate the device 12. In one embodiment, the reference pressure sensor and charging element can be combined into a single catheter. The ability to calibrate the implanted device 12 without subjecting the patient to an additional catheterization process may reduce the time and complexity associated with servicing the implanted device 12.

Figure 10:
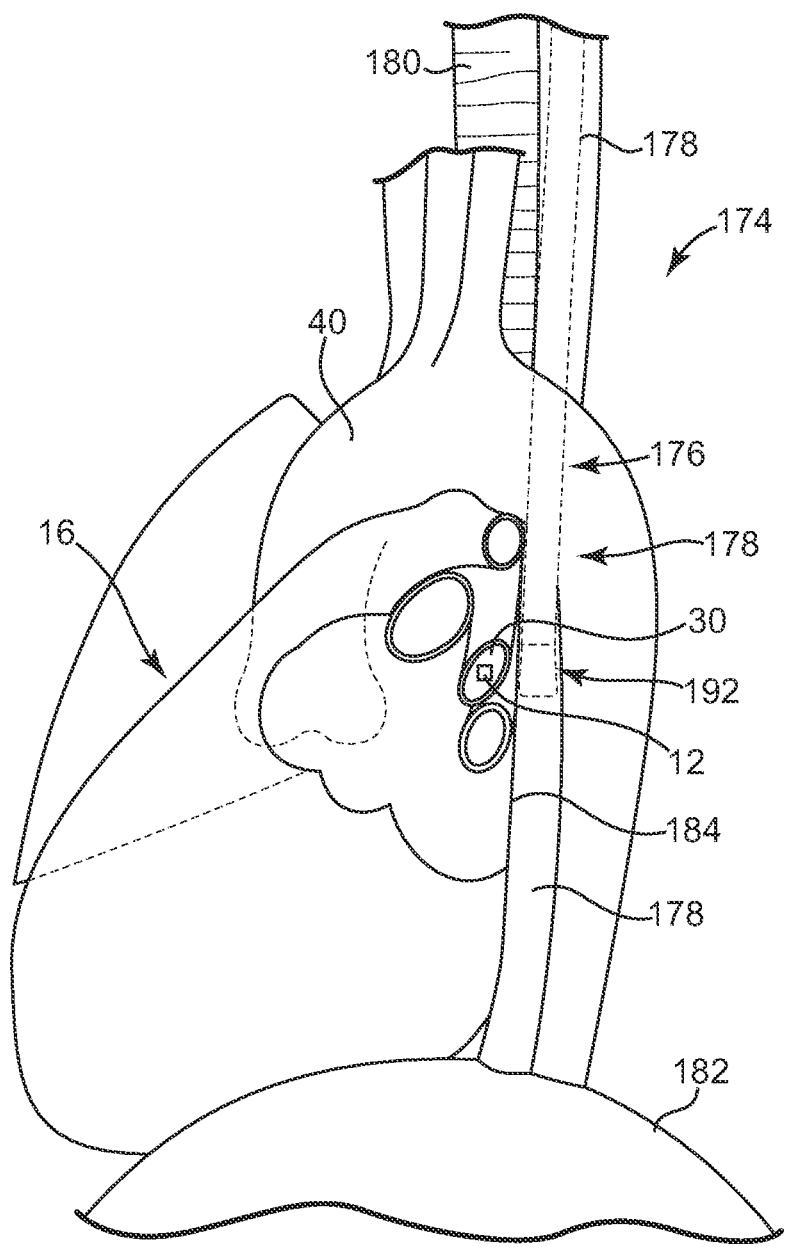
FIG. 10 is a schematic view showing another illustrative system for recharging a medical device implanted within a body lumen.

FIG. 10 is a schematic view of another illustrative system 174 for recharging a medical device 12 implanted within a body lumen using a transesophageal approach. In the embodiment of FIG. 10, a charging device 176 is inserted transesophageally into the esophagus 178 of the patient. The esophagus 178 is located posterior to the heart 16 and the airway 180, and extends downwardly to the stomach 182 at a location adjacent to the aorta 40 and the posterior wall 184 of the heart 16, as shown.

Figure 11:
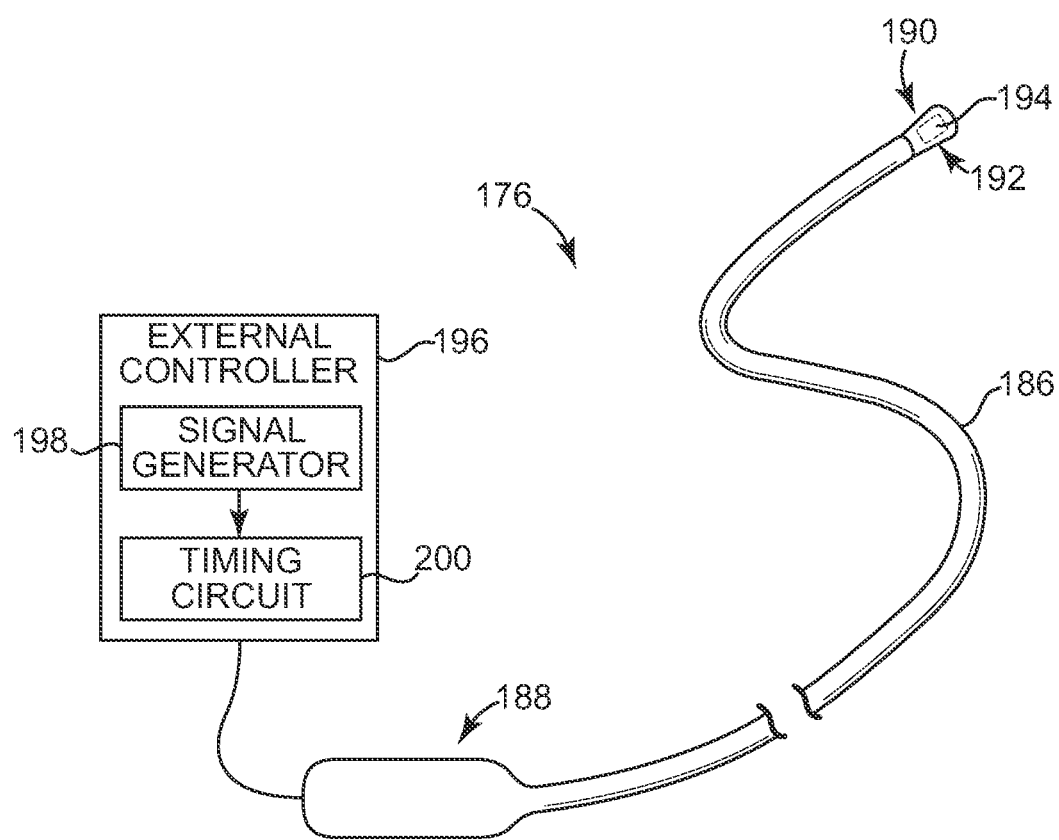
FIG. 11 is another view of the charging device of FIG. 10.

As can be further understood in conjunction with FIG. 11, the charging device 176 includes an elongate shaft 186 having a proximal section 188 and a distal section 190. The distal section 190 of the charging device 176 includes a cylindrically-shaped charging element 192 adapted to transmit energy from a position within the esophagus 178 to acoustically recharge an implanted device 12 located in an adjacent body lumen such as a pulmonary artery. In some embodiments, the charging element 192 comprises an array of ultrasonic transducers 194 which, when energized via an external controller 196, generate a radial, omnidirectional acoustic signal that is transmitted through the esophageal wall and into the adjacent pulmonary artery for recharging the implanted device 12. In some embodiments, the charging element 192 can include a polymeric coating or layer that matches the acoustic impedance of the charging element 192 with the surrounding fluid and tissue in the esophagus 178. In one embodiment, the charging element 192 and external controller 196 may be provided as part of a transesophageal echocardiogram (TEE) device.

The external controller 196 can include a signal generator 198 and a tuning circuit 200 that can be used to tune the frequency of the acoustic signal generated by the ultrasonic transducers 194 to a particular frequency or range of frequencies based on the resonance characteristics of the ultrasonic transducer elements used to transmit and receive the acoustic charging energy. In certain embodiments, for example, the signal generator 198 and tuning circuit 200 can be used to tune the ultrasonic transducer elements to a frequency of about 40 kHz, which can correspond to a resonance frequency of the ultrasonic transducer on the implanted device 12. In some embodiments, the signal generator 198 and tuning circuit 200 can be used to tune the ultrasonic transducer elements to operate over a desired range of frequencies (e.g., between about 10 kHz to 200 kHz). Other operating frequencies and frequency ranges are possible, however.

To recharge an implanted device 12 positioned in or near the heart 16, the distal section 190 of the charging device 176 can be inserted into the patient's esophagus 178 and advanced to a position within the esophagus 178 adjacent to the implantation location of the device 12. In those embodiments in which the implanted device 12 is located within a pulmonary artery 30, for example, the distal section 190 of the charging device 176 can be inserted into the esophagus 178 and positioned such that the charging element 192 is located in the mediastinum immediately posterior to the artery 30, as shown, for example, in FIG. 10. In some embodiments, the distal section 190 of the charging catheter 176 can be configured to substantially fill the lumen of the esophagus 178 such that a portion of the charging element 192 contacts the esophageal wall. In this position, the charging element 192 is located a short distance (e.g. 1 cm to 2 cm) from the adjacent artery 30, and provides a direct acoustic path between the charging element 192 and the implanted device 12. The esophagus 178 comprises primarily water and soft tissue, and is therefore acoustically matched with the impedance of the transducer elements, which helps to reduce losses in acoustic energy due to impedance mismatches.

Figure 12:
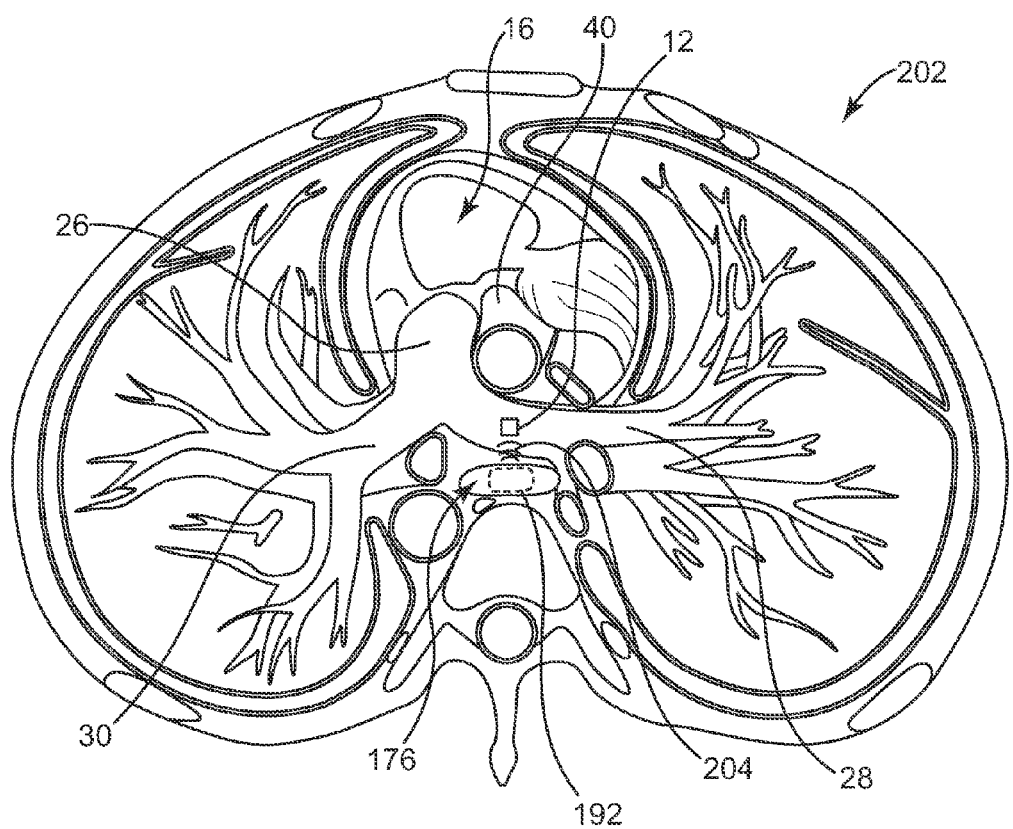
FIG. 12 is a transverse view of a patient's thorax, showing the insertion of the charging device of FIG. 10 in the esophagus adjacent to a medical device implanted within the right pulmonary artery.

Once the charging device 176 is positioned within the esophagus 178 adjacent to the body vessel or lumen containing the implanted device 12, the charging element 192 can be activated to generate an acoustic signal that travels through the esophageal wall. As can be further seen in a transverse view of the patient's thorax in FIG. 12, the charging element 192 can be positioned within the esophagus 178 at a location immediately adjacent to a device 12 implanted within the right pulmonary artery 28. In this position, the charging element 192 can be activated to generate an acoustic signal 204 that can be received by the implanted device 12 and converted into electrical energy for recharging the device 12. During recharging, the direct acoustic pathway and relatively short distance between the esophagus 178 and the artery 28 results in an increase in charge coupling efficiency between the charging element 192 and the implanted device 12. As with other embodiments discussed herein, this increase in efficiency reduces the overall time required to recharge the battery within the implanted device 12, and subjects the body to less energy than would otherwise be required to recharge the device 12 via an external recharging approach.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of recharging a medical device implanted within a body lumen of a body, the medical device including a first, rechargeable, power source and a receiver, the method comprising:
    delivering a distal section of a charging device to a location within the body adjacent to the implanted medical device, the charging device including a charging element operatively coupled to a second power source;
    activating the charging element and transmitting energy to the implanted medical device; and
    charging the first power source within the implanted medical device using the transmitted energy from the charging element.

2. The method of claim 1, wherein the charging element is coupled to the distal section of the charging device.

3. The method of claim 1, wherein the charging element is coupled to a proximal section of the charging device, and wherein transmitting energy to the implanted medical device includes transmitting energy through an interior lumen of the charging device.

4. The method of claim 1, wherein the charging element is an acoustic transducer, and wherein transmitting energy to the implanted medical device includes transmitting acoustic energy to an acoustic transducer coupled to the implanted medical device.

5. The method of claim 1, wherein the charging element is an electromagnetic transmitter, and wherein transmitting energy to the implanted medical device includes transmitting electromagnetic energy to an antenna or coil coupled to the implanted medical device.

6. The method of claim 1, wherein the charging device includes a means for cooling the charging element.

7. The method of claim 6, wherein the cooling means includes at least one cooling lumen within the charging device in fluid communication with a cooling medium.

8. The method of claim 1, wherein the charging device is a therapy delivery device, and further including providing therapy to the body.

9. The method of claim 1, wherein the charging device includes a focusing or collimating element adapted to focus the energy transmitted to the implanted medical device.

10. The method of claim 1, wherein delivering the distal section of the charging device to a location adjacent to the implanted medical device includes inserting the distal section of the charging device into the same body lumen as the implanted medical device.

11. The method of claim 1, wherein delivering the distal section of the charging device to a location adjacent to the implanted medical device includes inserting the distal section of the charging device into another body lumen adjacent to the body lumen containing the implanted medical device.

12. The method of claim 1, wherein delivering the distal section of the charging device to a location adjacent to the implanted medical device includes inserting the distal section of the charging device into the esophagus adjacent to the body lumen containing the implanted device.

13. The method of claim 1, wherein the charging device further includes a pressure sensor, and further including calibrating the implanted device using the pressure sensor.

14. The method of claim 1, wherein the charging device further includes a temperature sensor, and further including calibrating the charging device using the temperature sensor.

15. The method of claim 14, wherein the temperature sensor comprises a thermocouple wire embedded in a distal section of the charging device.

16. The method of claim 1, wherein the charging device includes a means for sensing electrical leakage from the charging element.

17. A method of recharging a medical device implanted within a body lumen of a body, the medical device including a first, rechargeable, power source and a receiver, the method comprising:
    delivering a distal section of a charging device to a location within the body adjacent to the implanted medical device, the charging device including an acoustic transducer operatively coupled to a second power source and at least one sensor;
    activating the acoustic transducer and transmitting an acoustic signal to the implanted medical device;
    sensing at least one parameter associated with the transmitted acoustic signal;
    adjusting at least one operating parameter of the acoustic transducer based at least in part on the at least one sensed parameter; and
    charging the first power source within the implanted medical device.

* * * * *